US00PP19272P2

(12) United States Plant Patent
Hambali

(10) Patent No.: US PP19,272 P2
(45) Date of Patent: Sep. 30, 2008

(54) ***CALATHEA* PLANT NAMED 'TWYCA0041'**

(50) Latin Name: ***Calathea* hybrid**
Varietal Denomination: TWYCA0041

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/974,055

(22) Filed: Oct. 11, 2007

(51) Int. Cl.
*A01H 5/00* (2006.01)

(52) U.S. Cl. ..... Plt./375

(58) Field of Classification Search ..... Plt./375
See application file for complete search history.

*Primary Examiner*—Annette H Para
(74) *Attorney, Agent, or Firm*—Jondle & Associates, P.C.

(57) ABSTRACT

A new *Calathea* plant particularly distinguished by tall upright, dense leafy growth habit with long-lasting, paper white bracted inflorescences which are held above and among the foliage, glossy, elliptical leaves with alternating bars of dark and lighter green which followed the primary veins and a thin band of silver green along the margin of the leaf is disclosed.

1 Drawing Sheet

Genus and species: *Calathea* hybrid.
Variety denomination: 'TWYCA0041'.

BACKGROUND OF THE NEW PLANT

The present invention comprises a new and distinct cultivar of *Calathea,* botanically known as *Calathea* hybrid, and hereinafter referred to by the cultivar name 'TWYCA0041'. The new cultivar originated from a hybridization made in Bogor, Indonesia. The female parent was an unnamed individual plant of *Calathea loesenerii* (unpatented). The male parent was a *Calathea roseopicta* named 'Cora' (U.S. Plant Pat. No. 10,898). A single plant selection was chosen for further evaluation and for asexual propagation in August 2000.

The new cultivar was first propagated in Apopka, Fla. and has been asexually reproduced repeatedly by tissue culture in Apopka, Fla. over four generations. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Broad, glossy elliptical leaves, with bars of dark green which follow the primary veins against a silver green background;
2. Long-lasting pink and green inflorescences displayed among the foliage; and
3. Upright, wider than tall, dense leafy, growth habit.

DESCRIPTION OF PHOTOGRAPHS

This new *Calathea* plant is illustrated by the accompanying photographs which show the overall plant habit including foliage of the plant and mature inflorescences; the colors shown are as true as can be reasonably obtained by conventional photographic procedures.

Figure 1:
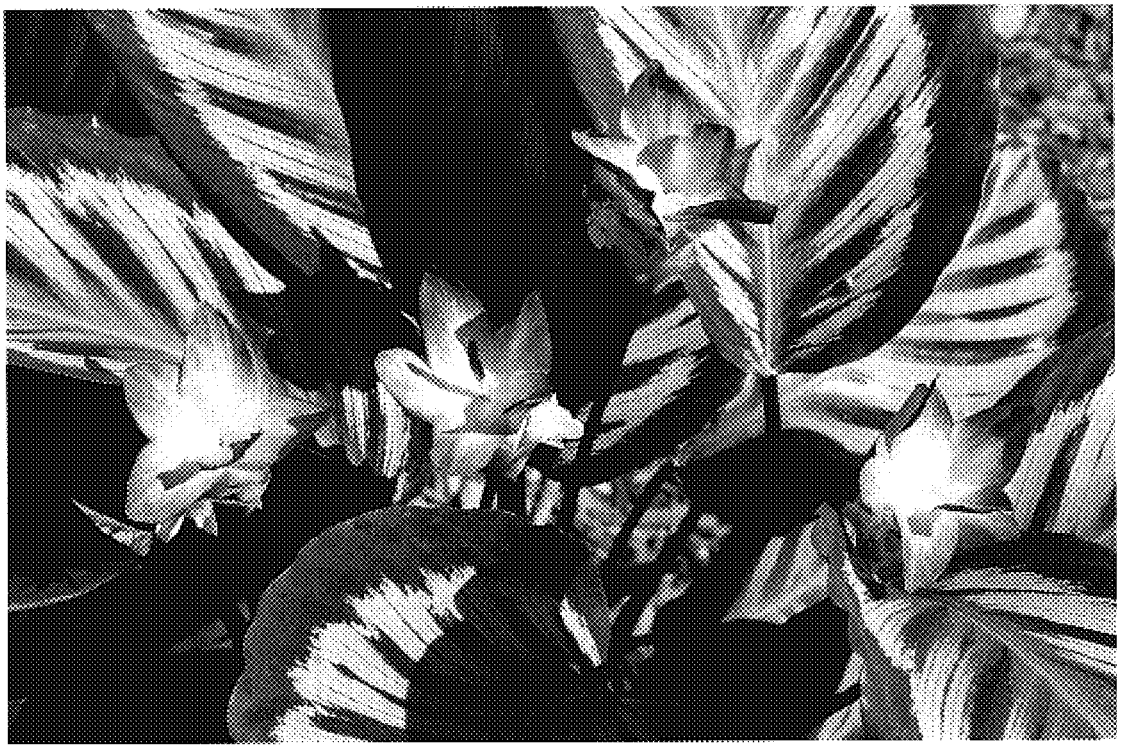

FIG. 1. The photograph shows the mature inflorescence.

Figure 2:
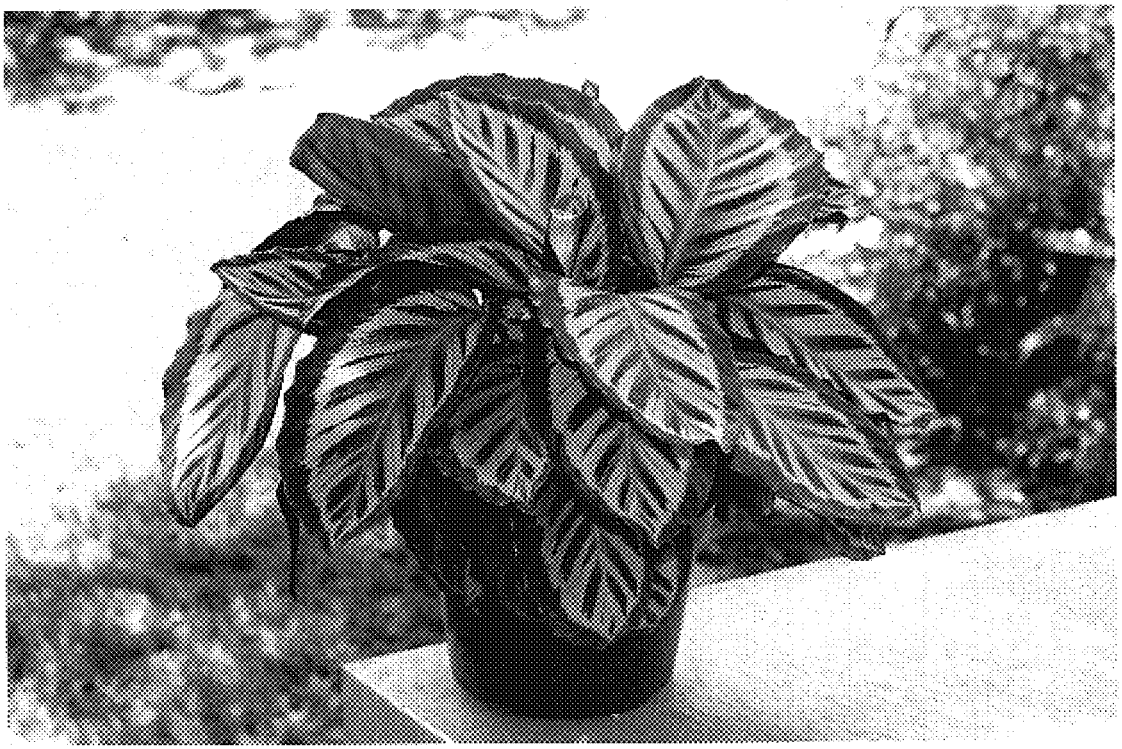

FIG. 2. The photograph shows the overall plant habit including the foliage.

DESCRIPTION OF THE NEW CULTIVAR

The following detailed description sets forth the distinctive characteristics of 'TWYCA0041'. The data which define these characteristics were collected from asexual reproductions carried out in Apopka, Fla. The data were obtained in February 2006 from 14-month old plants grown in 6-inch pots from a 13-week-old tissue culture derived liner. The plants were grown in a greenhouse with fiberglass panel siding with inflated double poly roof with a modine heating, fan and pad cooling system. The average day temperature ranged from 24° C. to 35° C. and the average night temperature ranged from 18° C. to 24° C. The light level was about 1500 FC. No photoperiodic treatments or growth retardants were used. Color references are to The Royal Horticultural Society Colour Chart, 2001 edition.

DETAILED BOTANICAL DESCRIPTION OF THE NEW PLANT

Classification:
- *Family.*—Marantaceae.
- *Botanical name.*—*Calathea* hybrid.
- *Common name.*—*Calathea.*

Parentage:
- *Female parent.*—An unnamed individual plant of *Calathea loesenerii* (unpatented).
- *Male parent.*—*Calathea roseopicta* plant named 'Cora' (U.S. Plant Pat. No. 10,898).

Growth:
- *General.*—Tropical flowering potted plant; plant is suitable for use in shaded tropical landscapes and indoors.
- *Time to flower.*—14 months to finish starting from a 13-week old liner from tissue culture.
- *Appropriate container.*—15 cm to 20 cm pots.

Plant description:

*Life cycle.*—Herbaceous perennial.

*Habit.*—Upright, wider than tall, inverted triangle, densely leafy; inflorescences upright among the foliage in the center of the plant; upright whorls of leaves arise from underground rhizome; rhizomaceous.

*Vigor.*—Typical of *Calathea;* progressive and consistent growth.

*Height* (*soil line to the top of the leaf canopy*).—49.0 cm to 56.0 cm.

*Spread.*—78.0 cm to 86.0 cm.

*Root color.*—RHS 164C to RHS 164D; tips RHS 145D to RHS 155C.

*Temperature tolerances.*—High temperature of 105° F. to a low temperature of 40° F.

Branches:

*Branching habit.*—Basal branching, rhizomaceous.

*Number.*—12 basal branches.

*Length.*—Variable depending upon age.

*Lateral branch diameter.*—1.0 cm to 1.3 cm.

Stems (rhizomes):

*Description.*—Cylindrical, round in traverse section.

*Aspect.*—Horizontal, underground rhizome becoming upturned, vertical at tip.

*Strength.*—Thick, tough and fibrous.

*Internode length.*—1.0 cm to 3.0 cm.

*Color.*—RHS N170C to RHS N170D to RHS 181D tinged with RHS 184D.

Leaves:

*Arrangement.*—Alternate, closely spaced in vertical ranks, rosette, with one to four leaves per lateral branch depending on age of the branch.

*Shape.*—Simple, broadly elliptical, side of leaf unrolling first wider than side unrolling last.

*Apex.*—Acuminate to cuspidate.

*Base.*—Obtuse.

*Margin.*—Entire, undulate.

*Size.*—Length; 25.0 cm. Width: 14.4 cm.

*Color.*—Immature leaf: Upper surface: Leaf Margin RHS 146B to RHS 147A with a very faint band of RHS 147B (lighter green); leaf center RHS 194D tinged with RHS 145D, with bars of RHS 147A following the primary veins; areas adjacent to the midrib RHS 146C. Lower surface: RHS 187A to RHS N186C. Mature leaf: Upper surface: Leaf margin RHS 147A with a very faint band of RHS 147B (light green); leaf center RHS 194C with bars of RHS 147A following the primary veins; areas adjacent to the midrib RHS 146C. Lower surface: RHS 187A to RHS N186C.

*Venation.*—Type: Pinnate. Color: Upper surface: RHS 146D midrib tinged with RHS 176B; primary veins RHS 147B. Lower surface: RHS 200B midrib, tinged with RHS N186C, primary veins RHS 187A to RHS 186C.

*Texture.*—Upper surface: Glossy to shiny, concave between primary veins resulting in a slightly textured look. Lower surface: Matte, glistening.

*Surface pubescence.*—Absent.

Petiole:

*Length* (*from basal attachment at rhizome to base of leaf*).—33.0 cm to 40.0 cm.

*Diameter.*—0.52 cm.

*Texture.*—Smooth.

*Color.*—RHS 187A tinged with RHS 200B.

*Petiole sheath.*—Encircles the rhizome and extends up the petiole to within 15.0 cm of the base of the leaf. Color: Outside: RHS 187B. Inside: Smooth, shiny RHS 183A.

*Cataphylls.*—Shape: Lanceolate. Apex: Acute. Base: Sessile, clasping rhizome. Length: 10.0 cm to 16.0 cm. Diameter (flattened): 3.0. Color: Outside: RHS N186C tinged with RHS 200B. Inside: Smooth shiny RHS 192B tinged with RHS 183A. Texture: Outside covered with short, fine pubescence.

Geniculum:

*General.*—The orientation of the leaf to the petiole is variable, as the geniculum bends. During the night and early morning the geniculum is straight, and the leaf is held nearly vertical above the petiole. During the day, the geniculum is bent, and the leaf is held about 90° to the petiole.

*Length.*—3.0.

*Diameter.*—0.52 cm.

*Color.*—RHS 187A tinged with RHS 200B.

Flower bud:

*Texture.*—Smooth.

*Size.*—Length: 2.0 cm. Diameter: 0.4 cm.

*Shape.*—Elongated, elliptic.

*Color.*—RHS 155D.

Inflorescence:

*Lastingness of the flowers on the plant.*—Individual flowers last about one day before shrivelling; one to about five flowers open simultaneously.

*Flowering season.*—Spring and fall.

*Arrangement.*—Inflorescence emerges from the center of the whorl of leaves; flowers emerge from short branch spikes under colored bracts atop a tall upright spike.

*Inflorescence type.*—Tall, upright, terminally bracted spike; bracts arranged in closely spaced vertical ranks occupying the upper 7.5 cm of the spike.

*Inflorescence height.*—37.0 cm.

*Inflorescence width.*—6.8 cm from tip to tip of bracts across top of inflorescence.

*Number of flowers per Inflorescence.*—84.

*Quantity of flowers and buds per plant.*—About 10 spikes present; about 840 flowers and buds per plant.

*Fragrance.*—Absent.

*Flowering habit.*—Tips of petals and staminods emerge from branch spikes under fertile bracts; flowers last about one day before fading and shrivelling; one to about five flowers open simultaneously per inflorescence over a period of about 6 weeks.

Flowers:

*General.*—Inflorescence persistent after senescence.

*Form.*—Tube-like; staminodes and petals curve outward.

*Aspect.*—Outward.

*Height* (*depth*).—2.8 cm.

*Diameter.*—1.8 cm across the face of the flower; tube of flower is 0.4 cm.

Petals:

*Appearance.*—Translucent, delicate, curved outward at tips.

*Arrangement.*—Tube like.

*Quantity.*—3.

*Shape.*—Narrow, elliptic.

*Margin.*—Entire.

*Apex.*—Acute.

*Length.*—2.6 cm.

*Width.*—0.4 cm.
*Texture* (*both surfaces*).—Smooth.
*Color* (*both surfaces*).—RHS 155D.
*Petal/staminode color.*—Fading to RHS 199C, ultimately becoming RHS 200A.

Sepal:
*Appearance.*—Translucent, pale white, crystalline.
*Arrangement.*—Tube like.
*Quantity.*—3.
*Shape.*—Narrow, elliptical to linear.
*Margin.*—Entire.
*Apex.*—Acute.
*Base.*—Acute.
*Length.*—1.5 cm.
*Width.*—0.3 cm.
*Texture* (*both surfaces*).—Smooth.
*Color* (*both surfaces*).—RHS 155C.

Peduncle:
*Length.*—34.0 cm.
*Diameter.*—0.45 cm.
*Angle.*—Straight upright.
*Strength.*—Tough, flexible.
*Texture.*—Smooth.
*Color.*—RHS N186C.

Bracts:
*General.*—Terminal bracts uppermost on raceme, subtended by fertile bracts with underlying branch spikes.
*Terminal bracts.*—Quantity: 9. Length: 3.8 cm. Width: 2.0 cm. Shape: Elliptic, tilted upward. Apex: Acute. Base: Acute. Margin: Entire, smooth. Color: Upper surface: RHS 186B to RHS 186C (pink) margins; center RHS 137B (green) towards tip; RHS 155A towards base. Lower surface: RHS 186A to RHS 186B tip and margins; RHS 137A (green) from the upper surface can be seen through the lower surface; RHS 155A at the base. Texture (both surfaces): Smooth.
*Fertile bracts.*—Quantity: 21. Length: 2.3 cm. Width: 2.8 cm. Shape: Broadly obovate. Apex: Emarginate. Base: Acute. Margin: Entire, smooth. Color (both surfaces): Margins white, center RHS 155C. Texture (both surfaces): Smooth.

Reproductive organs:
*Staminodes.*—Appearance: Thin crystalline, delicate. Arrangement: Tube-like, flared outward, reflexed at tips. Quantity: 3. Shape: Two are spatulate with emarginated tips, one short reduced, linear, cupped at tip. Margin: Entire. Length: 2.8 cm; Reduced staminode 2.2 cm. Width: 0.8 cm at widest point; Reduced staminode 0.3 cm. Texture (both surfaces): Smooth. Color: Spatulate staminodes RHS 155B flushed with RHS N87B; Reduced staminode RHS 155B flushed with RHS N87B.
*Stamen.*—Quantity: 1. Anther shape: Lanceolate. Length: 0.1 cm. Diameter: 0.05 cm. Color: RHS 10D (Yellow). Pollen amount: Sparse. Pollen color: RHS 155A.
*Pistil.*—Quantity: 1. Length: 2.6 cm. Stigma shape: Elliptic, cupped. Stigma color: RHS 155A. Style length: 2.5 cm. Style diameter: 0.1 cm. Style color: RHS 155A. Ovary: Inferior; 3 celled. Color: RHS 155A. Length: 0.15 cm. Diameter: 0.1 cm.

Fruit and seed set: Has not been observed.

Disease and insect resistance: Resistance and susceptibility is typical of the species.

COMPARISON WITH PARENTAL AND COMMERCIAL CULTIVARS

'TWYCA0041' differs from the female parent *Calathea loesenerii* (unpatented) in that 'TWYCA0041' has pink and green bracted inflorescences, while the female parent has pale pink to white bracted inflorescences. 'TWYCA0041' has broadly ovate leaves with attractive patterns, while the female parent has narrow, long leaves that are mostly green.

'TWYCA0041' differs from the male parent 'Cora' (U.S. Pat. No. 10,898) in that 'TWYCA0041' has pink and green bracted inflorescences which are displayed among the foliage, while 'Cora' has green, short scaped, inconspicuous bracts which are held mostly among and below the foliage.

'TWYCA0041' differs from the commercial *Calathea* names 'Illustris' (not patented) in that 'TWYCA0041' has pink and green bracted inflorescences which are displayed among the foliage, while 'Illustris' has green bracted, short scaped, inconspicuous bracts which are held mostly among and below the foliage. Additionally, 'TWYCA0041' has leaves with dark green bars which follow the primary veins against a silver-green background, while 'Illustris' has leaves with dark green bars which follow the primary veins against a pale green background.

I claim:

1. A new and distinct cultivar of *Calathea* plant as shown and described herein.

* * * * *